United States Patent [19]

Lezdey et al.

[11] Patent Number: 4,916,117

[45] Date of Patent: Apr. 10, 1990

[54] TREATMENT OF INFLAMMATION USING ALPHA 1-ANTICHYMOTRYPSIN

[76] Inventors: John Lezdey, 976 Kingston Dr., Cherry Hill, N.J. 08034; Allan Wachter, 7370 S. Bonarden La., Tempe, Ariz. 85283

[21] Appl. No.: 181,706

[22] Filed: Apr. 14, 1988

Related U.S. Application Data

[63] Continuation-in-part of Ser. No. 946,445, Dec. 24, 1986, abandoned.

[51] Int. Cl.[4] ...................... A61K 37/64; C07K 15/14
[52] U.S. Cl. ........................................... 514/8; 514/21; 530/395; 530/397
[58] Field of Search ...................... 514/21, 8; 530/380, 530/395, 397

[56] References Cited

U.S. PATENT DOCUMENTS

| | | | |
|---|---|---|---|
| 4,117,113 | 9/1978 | Allison et al. | 424/89 |
| 4,239,754 | 12/1980 | Sache et al. | 514/56 |
| 4,356,167 | 10/1982 | Kelly | 514/3 X |

OTHER PUBLICATIONS

Hospital Practice, Nov. 15, 1987, 97–116, MacDermott et al.
Diagnostic Histopathology, 4, 79–87, (1981), Meister et al.
Biochemistry, 22, 5055–5061, (1983), Chandra et al.

*Primary Examiner*—Howard E. Schain
*Attorney, Agent, or Firm*—John Lezdey

[57] ABSTRACT

A method for treating pulmonary and/or bowel inflammation in mammals by the administration of an effective amount of alpha 1-antichymotrypsin, its salt or derivative, and the pharmaceutical compositions therefor.

10 Claims, No Drawings

TREATMENT OF INFLAMMATION USING ALPHA 1-ANTICHYMOTRYPSIN

RELATED APPLICATIONS

This application is a continuation-in-part of application Ser. No. 946,445 filed Dec. 24, 1986, now abandoned.

FIELD OF THE INVENTION

The present invention relates to a method and composition for treating mammals afflicted with a certain inflammatory disease. More particularly, the present invention relates to the treatment of certain pulmonary and bowel diseases in mammals by administering alpha 1-antichymotrypsin, the salts or derivatives thereof.

BACKGROUND OF THE INVENTION

Alpha 1-antichymotrypsin is a naturally occurring protein. As disclosed by Meister P. Nathrath W, "Immunohistochemical Characterization of Histiocytic Tumors" *Design Histopathol*, 1981; 4: 79–87, alpha 1-antichymotrypsin is present within malignant macrophages and has been proposed as a useful immunohistochemical marker for cells of the monocyte/macrophage series.

Chandra et al in their paper entitled, "Sequence Homology Between Human alpha 1-Anitchymotrypsin, Alpha 1-Antitrypsin, and Antithrombin III, *Biochemistry*, Vol. 22, No. 22, Oct. 25, 1983, p. 5055–5061, which is incorporated herein by reference, discloses one method for the isolation of Alpha 1-antichymotrypsin for use in the invention.

Alpha 1-antichymotrypsin is a plasma protease inhibitor synthesized in the liver. It is a single glycopeptide chain of approximately 58,000 daltons and belongs to a class of serine protease inhibitors with an apparent affinity toward chymotrypsin-like enzymes. Alpha 1-antichymotrypsin is structurally related to alpha 1-antitrypsin.

Belgian Patent No. 830,620 (1975), which is herewith incorporated by reference, discloses and claims immunologically active compositions characterized by an immunologically effective agent incorporated in a negatively charged liposome. Some of the agents thus encapsulated include virus antigens, bacterial antigens, and the like.

U.S. Pat. No. 4,356,167 to L. A. Kelly, which is incorporated herein by reference, discloses liposome drug delivery systems which may be used in connection with the present invention.

U.S. Pat. No. 4,239,754 to Sache et al, which is incorporated herein by reference, discloses liposome compositions for oral administration.

SUMMARY OF THE INVENTION

The present invention relates to a method for treating inflammatory conditions of the pulmonary tract and the bowels in mammals including humans by the administration of alpha 1-antichymotrypsin, the salts or derivatives thereof in a suitable pharmaceutical composition.

Among the inflammatory conditions which may be treated with alpha 1-antichymotrypsin there are included inflammations of the tracheobronchial tree such as bronchitis, emphysema, chronic obstructive pulmonary disease, Chronic Granulomatous Lung Disease i.e. Sarcoid, inflammatory diseases of the bowel including regional enteritis (Crohn's Disease) and colitis.

The use of alpha 1-antichymotrypsin has been especially useful in the treatment of the various inflammatory conditions including those which are induced by virus and bacterial infections. The compositions of the invention have also been found to cause vasoconstriction which in inflammation decreases swelling and redness.

The drug of the invention may be cloned by conventional techniques utilizing an antibody probe. Preferably, an antibody against Cl-esterase inhibitor or alpha 1-antichymotrypsin is utilized as the probe. It has been found that the Cl-esterase inhibitor is not cross-reactive with any other native proteins in human serum as examined by immuno-diffusion assays. The recombinant gene product of the invention is especially useful since it is free of contaminating viruses when produced.

The activity of alpha 1-antichymotrypsin was determined by Enzyme Kinetic Analysis using association and competitive experiments. When run against Mast Cell Chymase, the subject drug was noted as being at least 30% active. When tested against Cathepsin-G, there was an association constant of $6 \times 10^7$. In a competitive test against Mast Cell Chymase there was an association constant of $3 \times 10^7$.

The salts and derivatives may be formed utilizing conventional techniques associated with other proteins without effecting the utility of the compound. There may be prepared the alkali metal salts, acid-addition salts, and esters similar to other proteins or peptides.

It is an object of the invention to provide an anti-inflammatory composition which can be used as a prophylaxis and/or in treatment of existing inflammatory pulmonary or bowel diseases.

It is another object of the invention to provide a composition for smokers which can prevent or treat irritations arising from tobacco use.

It is a further object of the invention to provide an anti-inflammatory composition for pulmonary and bowel diseases which is well tolerated by the human body and is free of side effects.

It is a yet still further object of the invention to provide a method and a composition for treating inflammatory conditions such as bronchitis, emphysema and colitis.

DETAILED DESCRIPTION OF THE PRESENT INVENTION

The objects of the present invention can be achieved by the administration of purified alpha 1-antichymotrypsin in suitable pharmaceutical form to patients suffering from inflammatory conditions of the pulmonary tract and bowels.

The present invention provides a pharmaceutical composition which comprises the compound of this invention and a pharmaceutically acceptable carrier.

The compositions of the invention include those in a form adapted for oral, parenteral use inhalation techniques, and the like and may be used for the treatment of the inflammation of the pulmonary tract and/or bowels in mammals including humans.

Suitable forms of the compositions of this invention include tablets, capsules, creams, syrups, suspensions, solutions, reconstitutable powders and sterile forms suitable for injection of infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form.

The injectable solution of the compound of this invention may be made up in a sterile pyrogen-free liquid such as water, aqueous ethanol or the like.

An alternative approach to administering the compounds of this invention is to utilize an injectable suspension. Such suspensions may be made up in sterile water; sterile saline or the like and may also contain suspending agents such as polyvinylpyrrolidone, lecithin or the like (for example in the manner described in Belgian Patent No. 839109). Alternatively, such compositions may be prepared in an acceptable oily suspending agent such as arachis oil or its equivalent.

Unit dose compositions comprising a compound of this invention adapted for oral administration form a further suitable composition aspect of this invention. Orally administrable compositions are of use as synergistically effective blood levels can be expected at high doses and at lower doses such compositions may be used to treat inflammations localized in the gastro-intestinal tract.

Suitably the weight of the compound of this invention in a unit dosage form of this invention will be from 50 to 500 mg and more suitably from 50 to 250 mg.

In general the total quantity of anti-inflammatory agent present in a composition of this invention will not be greater than 1500 mg and will usually be between 100 and 1000 mg.

Normally between 500 and 3000 mg of the compositions of the invention will be administered each day of treatment (to an average 70 kg adult). Similar amounts may be administered to prevent the occurrence of the condition.

In the treatment of chronic cases of inflammatory lung conditions wherein the cells express proteases, such as in the case of emphysema, the patient is typically administered intravenously 15 to 90 mg of alpha 1-antichymotrypsin compound per kilogram of body weight weekly at a rate of 2 mg per kilogram per minute. The treatment is continued for a period of time until there is a reversal of the biochemical abnormalities in serum and lung fluid that characterizes the disorder. The treatment may be followed up by administration of the drug by inhalation to more rapidly promote healing. For use in the prevention of the disease, the drug may be administered orally or by inhalation techniques on a weekly basis. This weekly treatment is believed to aid smokers from incurring the inflammation of the pulmonary tract which is commonly associated with smoking.

The active ingredient of the invention may be incorporated into a metered-dose aerosol unit containing a microcrystalline suspension of the drug in a mixture of inert halogenated hydrocarbon propellants with oleic acid. Preferred propellants are trichloromonofluoromethane and dichlorodifluoromethane or mixtures thereof. Each unit has a molecular proportion of active ingredient to the halogenated hydrocarbon between 3:1 and 3:2. Each actuation of the aerosol cannister delivers a quantity of drug equivalent to 42–90 mcg.

The inhaler is useful for prophylactic use as well as for direct treatment of pulmonary diseases or inflammations.

It has been particularly advantageous to administer the alpha 1-antichymotrypsin compound in liposomes. When the drug is administered by intravenous injection in liposome form there is a more rapid intake of the drug. This rapid intake is particularly useful in connection with pulmonary inflammations.

The drug in liposomes can be administered orally in order to transgress the gastric barrier and prevent disintegration in the stomach. The liposome form also provides a delay effect so as to provide prolonged activity.

Any non-toxic physiologically acceptable metabolizable lipid capable of forming liposomes may be used for carrying out the invention. The liposomes may be prepared as disclosed by W. R. Hargreaves and D. W. Deamer, "Conference on Liposomes and Their Uses in Biology and Medicine", Sept. 14–16, 1977, N.Y. Academy of Sciences, which is herein incorporated by reference.

The following examples further illustrate the practice of this invention, but are not intended to be limiting thereof. It will be appreciated that the selection of actual amounts of specific alpha 1-antichymotrypsin to be administered to any individual patient (human or animal) will fall within the discretion of the attending physician (or veterinarian) and will be prescribed in a manner commensurate with the appropriate risk:benefit ratio for that particular patient. Appropriate dosages will depend on the patient's age, weight, sex, stage of disease and like factors uniquely within the purview of the attending physician. The compositions can be administered via the G.I. tract, parenterally, e.g., by i.v. infusion, and by injection.

EXAMPLE I

Following the procedure of U.S. Pat. No. 4,239,754, a lipid phase made up of the three components lecithin, cholesterol and dicetyl-phosphate in a molar ratio of 7:2:1 is prepared with 2.6 g of lecithin, 0.04.4 g. of cholesterol and 0.31 g dicetyl-phosphate by dissolving in 50 ml of chloroform and the solution evaporated, 4.0 g of alpha 1-antichymotrypsin is dissolved in 50 ml of an acid buffer (citric acid) pH 7.5–8.0 and added to the phospholipids. The mixture is then subjected to sonification for 10 seconds.

In place of cholesterol, any sterol capable of forming liposomes may be utilized, such as, desmosterol, estradiol, B-sitosterol, and the like.

The composition is effective for treating bowel diseases.

EXAMPLE II

Pill are prepared as follows:

| | |
|---|---|
| Alpha 1-antichymotrypsin | 216 mg |
| Phospholipon 100 | 400 mg |
| aerosil | 50 mg |
| Na-carboxymethylcellulose | 16 mg |
| Cuttina H | 12 mg |
| microcrystalline cellulose | 150 mg |

The substances listed above are mixed, pressed and the items so pressed are coated in a manner known per se with 20 mg of hydroxypropylmethylcellulosephthalate in a coating drum.

The composition is especially useful for treatment of bowel diseases such as colitis.

EXAMPLE III

Capsules are prepared as follows:

| | |
|---|---|
| Alpha 1-antichymotrypsin | 108 mg |
| Phospholipon 80 | 200 mg |
| talcum | 3 mg |
| magnesiumstearate | 3 mg |
| microcrystalline cellulose | 100 mg |
| aerosil | 25 mg |

The substances listed above are granulated and filled into capsules (500 mg hard-gelatin capsules).

In place of alpha 1-antichymotrypsin there may be used any one of the water-soluble salts thereof.

EXAMPLE IV

Microcrystalline alpha 1-antichymotrypsin is suspended in oleic acid and added into a metering aerosol cannister together with trichloromonofluoromethane and dichlorodifluoromethane so that the unit has a molecular proportion of alpha 1-antichymotrypsin to the propellant between 3:1 and 3:2. The unit delivers a quantity of drug equivalent to 42 mcg.

I claim:

1. A method for treating the symptoms of pulmonary and/or bowel inflammations in a mammal or the prophylaxis treatment therefor which comprises administering an effective amount of alpha 1-antichymotrypsin, the derivatives or salts thereof.

2. The method of claim 1 wherein said inflammation is caused by emphysema.

3. The method of claim 1 wherein alpha 1-antichymotrypsin is administered in an effective amount to prevent or inhibit inflammation.

4. The method of claim 1 wherein alpha 1-antichymotrypsin is administered in an amount effective to cause vasoconstriction at the site of the inflammation.

5. The method of claim 1 wherein alpha 1-antichymotrypsin is administered by inhalation techniques in an amount sufficient to inhibit bronchial inflammation.

6. The method of claim 5 wherein the condition treated is colitis.

7. The method of claim 1 wherein the inflammatory condition is brochitis.

8. A method for treating a mammal afflicted with an inflammatory disease of the lungs, the cells of which express proteases, which comprises administering to said mammal alpha 1-antichymotrypsin in an effective amount to prevent proliferation of said cells in vivo.

9. The method of claim 8 wherein alpha 1-antichymotrypsin is administered in unit dosage form of about 50 to 500 mg.

10. A pharmaceutical composition in inhalation form for treating the symptoms of pulmonary inflammation comprising a microcrystalline suspension of an effective amount of alpha 1-antichymotrypsin and an inert propellant.

* * * * *